US009668710B2

(12) United States Patent
Ruijters et al.

(10) Patent No.: US 9,668,710 B2
(45) Date of Patent: Jun. 6, 2017

(54) TRACKING BRAIN DEFORMATION DURING NEUROSURGERY (75) Inventors: Daniël Simon Anna Ruijters, Eindhoven (NL); Drazenko Babic, Best (NL)

(73) Assignee: Koninklijke Philips N.V., Eindhoven (NL)

(*) Notice: Subject to any disclaimer, the term of this patent is extended or adjusted under 35 U.S.C. 154(b) by 55 days.

(21) Appl. No.: 14/005,620

(22) PCT Filed: Mar. 1, 2012

(86) PCT No.: PCT/IB2012/050971
§ 371 (c)(1),
(2), (4) Date: Sep. 17, 2013

(87) PCT Pub. No.: WO2012/127345
PCT Pub. Date: Sep. 27, 2012

(65) Prior Publication Data
US 2014/0003698 A1    Jan. 2, 2014

(30) Foreign Application Priority Data
Mar. 18, 2011  (EP) .................................. 11158830

(51) Int. Cl.
*G06T 7/33*    (2017.01)
*A61B 6/00*    (2006.01)

(52) U.S. Cl.
CPC .............. *A61B 6/501* (2013.01); *A61B 6/461* (2013.01); *A61B 6/467* (2013.01); *A61B 6/5217* (2013.01);
(Continued)

(58) Field of Classification Search
None
See application file for complete search history.

(56) References Cited

U.S. PATENT DOCUMENTS 5,633,951 A * 5/1997 Moshfeghi ........... G06K 9/6207
375/E7.084
5,954,648 A    9/1999 Van Der Brug
(Continued)

FOREIGN PATENT DOCUMENTS

JP    2003339670 A    12/2003
WO    2010037850 A2    4/2010

OTHER PUBLICATIONS

Reinertsen, I. et al "Validation of Vessel-Based Registration for Correction of Brain Shift", Sciencedirect, Medical Image Analysis, vol. 11, 2007, pp. 374-388.
(Continued)

*Primary Examiner* — Tsung-Yin Tsai (57) ABSTRACT

An imaging system for tracking brain deformation, a method for tracking brain deformation, a method of operating a device for tracking brain deformation are disclosed. A first 3D representation (112) of a cerebrovascular vessel structure of a region of interest of an object is provided (110), and (114) a second 3D representation (116) of the cerebrovascular vessel structure are used to determine brain deformation. At least a part of the first 3D representation is elastically three-dimensionally registered (118) with at least a part of the second 3D representation. A deformation field (122) of the cerebrovascular vessel structure is determined (120) based on the elastic registration. The determined vessel deformation is applied (124) to a brain structure representation to determine a deformation (126) of the cerebral structure.

11 Claims, 10 Drawing Sheets (52) U.S. Cl.
CPC .......... *A61B 6/5235* (2013.01); *A61B 6/5247* (2013.01); *G06T 7/33* (2017.01); *G06T 2207/10072* (2013.01); *G06T 2207/30016* (2013.01); *G06T 2207/30101* (2013.01)

(56) References Cited

U.S. PATENT DOCUMENTS

| | | | | |
|---|---|---|---|---|
| 7,948,503 | B2* | 5/2011 | Shekhar | G01T 1/1611 345/648 |
| 8,666,128 | B2* | 3/2014 | Chaney | G06K 9/621 382/128 |
| 2005/0089213 | A1* | 4/2005 | Geng | G06K 9/00214 382/154 |
| 2007/0021669 | A1* | 1/2007 | Miga | G06T 7/38 600/425 |
| 2008/0123927 | A1* | 5/2008 | Miga | A61B 90/36 382/131 |
| 2008/0247622 | A1* | 10/2008 | Aylward | A61B 90/36 382/131 |
| 2008/0317317 | A1* | 12/2008 | Shekhar | G06T 3/0081 382/131 |
| 2011/0026794 | A1* | 2/2011 | Sundar | G06K 9/44 382/131 |
| 2011/0257514 | A1* | 10/2011 | Bucki | G06T 7/0038 600/420 |
| 2015/0335390 | A1 | 11/2015 | Gill | |

OTHER PUBLICATIONS

Clatz, Olivier et al "Robust Nonrigid Registration to Capture Brain Shift From Intraoperative MRI", IEEE Transactions on Medical Imaging, vol. 24, No. 11, Nov. 2005, pp. 1417-1427.

Aylward, Stephen R. et al "Registration and Analysis of Vascular Images", Intl Journal of Computer Visiion, vol. 55, 2003, pp. 123-138.

Gholipour, Ali et al "Brain Functional Localization: A Survey of Image Registration Techniques", IEEE Transactions on Medical Imaging, vol. 26, No. 1, 2007, pp. 427-451.

Sun, Hai et al "Using Cortical Vessels for Patient Regisration during Image-Guided Neurosurgery—A Phantom Study", Medical Imaging 2003: Visualization Image-Guided Procedures and Display, vol. 5029.

Kita, Yasuyo et al "Real-Time Registration of 3D Cerebral Vessels to X-Ray Angiograms", Medical Image Computing and Computer Assisted Intervention 1998, vol. 1496.

* cited by examiner

TRACKING BRAIN DEFORMATION DURING NEUROSURGERY

CROSS-REFERENCE TO PRIOR APPLICATIONS

This application is the U.S. National Phase application under 35 U.S.C. §371 of International Application No. PCT/IB2012/050971, filed on Mar. 1, 2012, which claims the benefit of European Patent Application No. 11158830.7, filed on Mar. 18, 2011. These applications are hereby incorporated by reference herein.

FIELD OF THE INVENTION

The present invention relates to the determination of brain deformation. The invention relates in particular to a device for tracking brain deformation, an imaging system for tracking brain deformation, a method for tracking brain deformation, a method of operating a device for tracking brain deformation, as well as to a computer program element and a computer readable medium.

BACKGROUND OF THE INVENTION

For neurological interventions, image information is provided to a user about a region of interest. For example, U.S. Pat. No. 5,954,648 describes that images which have been collected earlier are shown to the surgeon during an operation. However, during neurosurgery, for example during neuro-operations or neuro-interventions, for example, the leakage of the cerebral spinal fluid can result in a local deformation of the brain during treatment. As a consequence, image data acquired before the treatment may be at least in local misalignment with the current brain structure.

SUMMARY OF THE INVENTION

It has been shown that an exact knowledge of the deformation of the brain is important and crucial for following treatment procedures.

Thus, there exists a need for providing enhanced information about the current brain deformation.

The object of the present invention is solved by the subject-matter of the independent claims, wherein further embodiments are incorporated in the dependent claims.

It should be noted that the following described aspects of the invention apply also for the device for tracking brain deformation, the imaging system for tracking brain deformation, the method for tracking brain deformation, the method of operating a device for tracking brain deformation, the computer program element as well as the computer readable medium.

According to a first aspect of the invention, a device for tracking brain deformation is provided, comprising a processing unit and an interface unit. The interface unit is adapted to provide a first 3D representation of a cerebrovascular vessel structure of a region of interest of an object to the processing unit. The interface unit is also adapted to provide a second 3D representation of the cerebrovascular vessel structure to the processing unit. The processing unit has a register unit adapted to elastically three-dimensionally register at least a part of the first 3D representation with at least a part of the second 3D representation. The processing unit has a determination unit adapted to determine a deformation field of the cerebrovascular vessel structure based on the elastic registration. The processing unit has an application unit adapted to apply the determined vessel deformation to a brain structure representation to determine a deformation of the cerebral structure.

For example, the first 3D representation is based on pre-operative image data and the second 3D representation is based on intra-operative image data.

The first 3D representation may also be based on previously acquired image data, belonging to regularly scheduled examination image data, and the second 3D representation is based on examination image data.

The first 3D representation of the cerebrovascular vessel structure may origin from an external dataset, e.g. CTA, MRA.

According to an exemplary embodiment of the present invention, the application unit is adapted to apply the determined deformation of the cerebral structure to planning data for an intervention of the cerebral structure to generate deformation adjusted planning data.

According to a further exemplary embodiment of the invention, the processing unit comprises an extrapolation unit adapted to extrapolate the determined vessel deformation to the brain structure representation, wherein the brain structure representation comprises a vessel structure and a lobe structure comprising a number of convolutions in which the vessels are arranged. The application unit is adapted to apply the deformation to the lobes only.

According to a second aspect of the invention, an imaging system for tracking brain deformation is provided, comprising a device for tracking brain deformation according to one of the above-mentioned aspects or exemplary embodiments, and an image acquisition device. The image acquisition device is adapted to acquire 3D image data for the first and for the second representation. The processing unit comprises a 3D image data generation unit adapted to generate the first and second representation from the 3D image data. Further, the image acquisition device is adapted to acquire the second image data in a contactless manner.

For example, the image acquisition device is an X-ray image acquisition device adapted to acquire 3D X-ray image data.

For example, the image acquisition device is a non X-ray modality, like an MR image acquisition device adapted to acquire 3D MR image data.

According to a third aspect of the invention, a method for tracking brain deformation is provided, comprising the following steps: In a first provision step, a first 3D representation of a cerebrovascular vessel structure of a region of interest of an object is provided. In a second provision step, a second 3D representation of the cerebrovascular vessel structure is provided. In a registration step, at least a part of the first 3D representation is elastically three-dimensionally registered with at least a part of the second 3D representation. In a determination step, a deformation field of the cerebrovascular vessel structure is determined based on the elastic registration. Further, in an application step, the determined vessel deformation is applied to a brain structure representation in order to determine a deformation of the cerebral structure.

For example, pre-operative anatomical data and/or functional data is provided for the region of interest, and the determined deformation of the cerebral structure is applied to the anatomical data and/or functional data to generate deformation adjusted anatomical data and/or deformation adjusted functional data.

According to a fourth aspect of the invention, a method of operating a device for tracking brain deformation is provided, wherein a processing unit provides a first 3D representation of a cerebrovascular vessel structure of the region of interest of an object. The processing unit provides a second 3D representation of the cerebrovascular vessel structure. The processing unit elastically three-dimensionally registers at least a part of the first 3D representation with at least a part of the second 3D representation. The processing unit determines a deformation field of the cerebrovascular vessel structure based on the elastic registration. The processing unit applies the determined vessel deformation to a brain structure representation to determine a deformation of the cerebral structure.

It can be seen as the gist of the invention to provide an elastic three-dimensional registration in order to achieve the local displacements of the current brain structure. The elastic registration is performed for the vessel structure or vasculature. The determined deformation of the vessel is then applied to the brain structure itself. In other words, the present invention provides performing the elastic registration for the vessel structure first, and not directly for the brain structure. The determined deformation is then applied, or transformed, to the brain itself, because the vessels in the brain are contained within the convolutions, and because local displacements of vessels in the brain allow for accurately estimating the local brain deformation. The brain deformation may then be used to adjust pre-procedural planning to the actual current situation. The brain deformation information may also be fed into an external navigation system, for example for steering an interventional device. The image data for the 3D representation, in particular for the second representation are provided with contactless image acquisition, for example with X-ray imaging and thus do not affect the brain deformation itself.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

FIGS. 11 to 18 illustrate further examples of a method for tracking brain deformation according to exemplary embodiments of the invention.

DETAILED DESCRIPTION OF EMBODIMENTS

Figure 1:
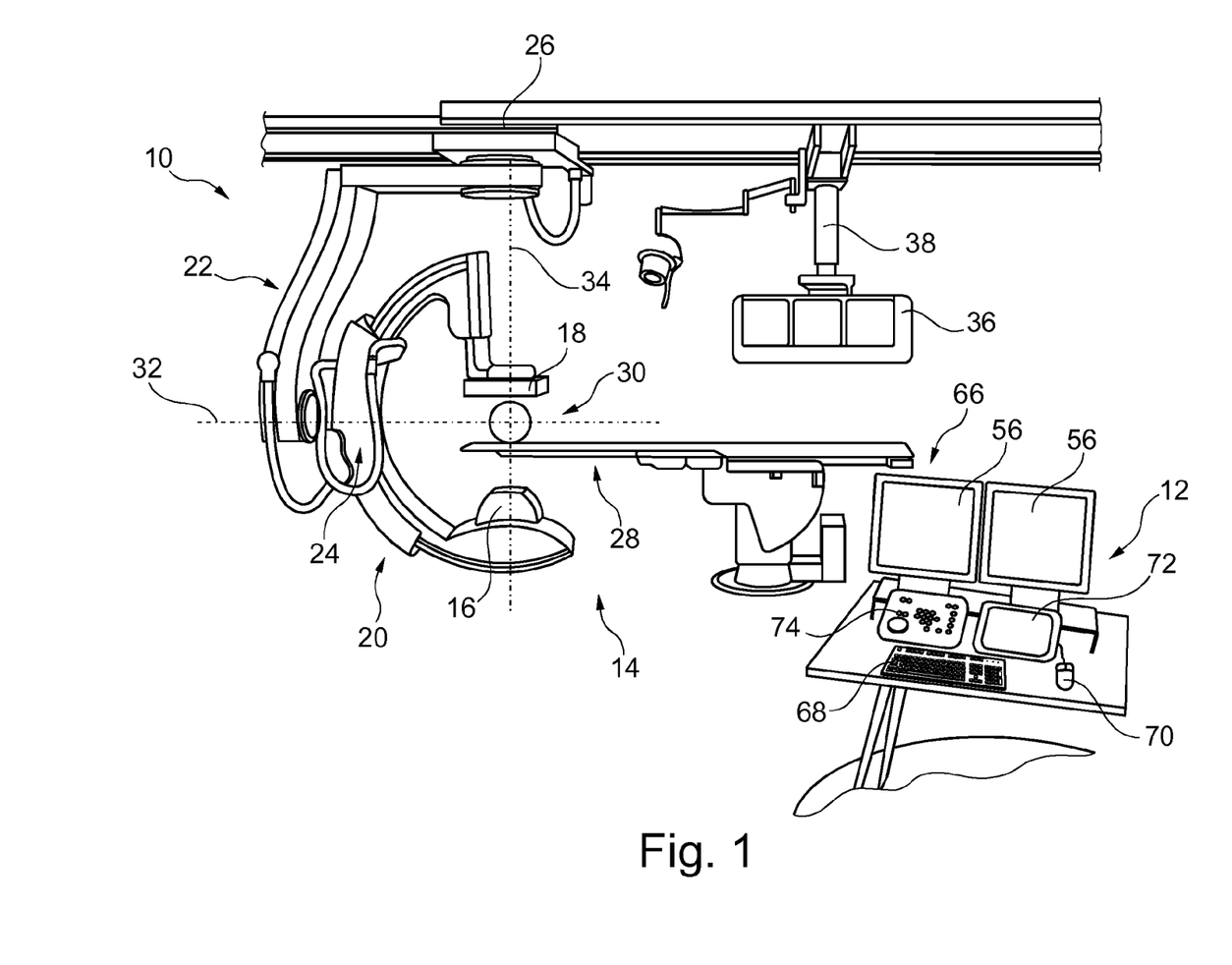
FIG. 1 illustrates an imaging system for tracking brain deformation according to an exemplary embodiment of the invention.

FIG. 1 schematically illustrates an imaging system 10 for tracking brain deformation. The system 10 comprises a device 12 for tracking brain deformation and an image acquisition device 14. The device 12 for tracking brain deformation will be explained in more detail with reference to FIGS. 2 to 9.

For example, the image acquisition device is an X-ray image acquisition device adapted to acquire 3D X-ray image data.

According to a further embodiment, not shown, the image acquisition device is an MR image acquisition device adapted to acquire 3D MR image data.

The X-ray image acquisition device 14 comprises an X-ray source 16 and a detector 18. The detector 18 and the X-ray source 16 are arranged on opposing ends of a C-arm structure 20. The C-arm structure 20 is mounted to a suspending structure 22 with a rotatable and slideable attachment 24. The suspending structure 22 is mounted to a support structure 26, for example attached to a ceiling of an operational room in a hospital.

Further, a table 28 is provided to receive an object of interest 30, for example a patient. The table 28 can be provided to be adaptable in a horizontal direction as well as in the vertical direction.

Thus, the object of interest 30 can be arranged between the X-ray source 16 and the detector 18.

By providing the C-arm structure to be rotatable around a horizontal axis 32, and also to be rotatable via the ceiling mounting around a vertical axis 34, it is possible to acquire image information about the object 30 from different directions.

Further, a display unit 36 is provided in the vicinity of the table, for example being suspended with a mounting structure 38 from the ceiling.

The X-ray image acquisition device 14 is adapted to acquire 3D X-ray image data for a first and second representation, which will be explained in relation with the device 12 for tracking brain deformation and referring to FIG. 2 et seq.

It must be noted that the above described embodiment of the X-ray imaging system 10 is shown with a C-arm structure. However, according to the present invention, the X-ray imaging system 10 can also provided, for example, as a CT system, or any other X-ray imaging system capable of acquiring three-dimensional X-ray image data of the object 30.

Figure 2:
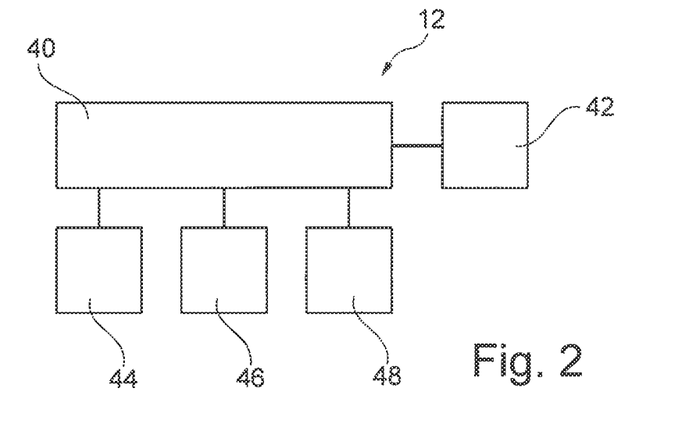
FIG. 2 schematically illustrates a device for tracking brain deformation according to an exemplary embodiment of the invention.

FIG. 2 schematically illustrates the device 12 for tracking brain deformation according to the present invention. The device 12 for tracking brain deformation comprises a processing unit 40 and an interface unit 42.

The interface unit 42 is adapted to provide a first 3D representation of a cerebrovascular vessel structure of a region of interest of an object to the processing unit 40. The interface unit 42 is also adapted to provide a second 3D representation of the cerebrovascular vessel structure to the processing unit 40.

For example, the first 3D representation is based on pre-operative image data and the second 3D representation is based on intra-operative image data.

The processing unit 40 has a register unit 44, which is adapted to elastically three-dimensionally register at least a part of the first 3D representation with at least a part of the second 3D representation.

The processing unit has further a determination unit 46, which is adapted to determine a deformation field of the cerebrovascular vessel structure based on the elastic registration.

The processing unit also has an application unit 48, which is adapted to apply the determined vessel deformation to a brain structure representation to determine a deformation of the cerebral structure.

For example, the interface unit 42 is adapted to provide image data from different data acquisition devices, or adapted to provide different types of 3D data acquired with one or more image acquisition devices.

The interface unit 42 can be adapted to provide the deformation of the cerebral structure for further procedures (not further shown).

Figure 3:
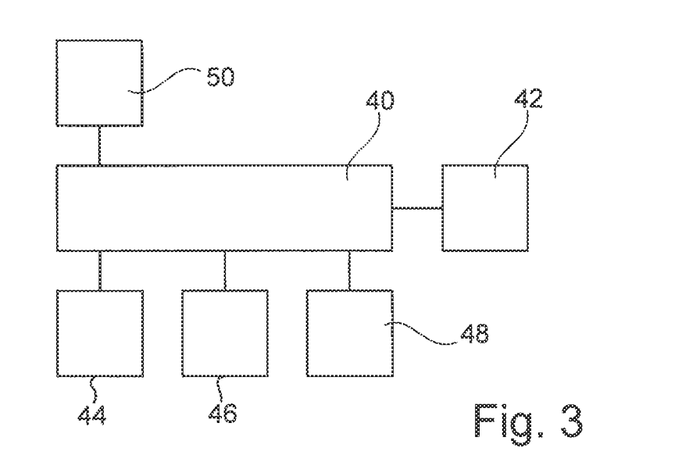
FIGS. 3 to 10 illustrate further examples of a device for tracking brain deformation according to exemplary embodiments of the invention.

FIG. 3 shows a further example of the processing unit 40 with a mapping unit 50, which is adapted to map the first and the second representation for the elastic registration.

For example, the first 3D representation is based on pre-operative image data and the second 3D representation is based on intra-operative image data.

According to the present invention, the term "operation" is associated with open surgery and the term "intervention" is associated with endovascular treatment as minimal invasive therapy. However, the present invention relates to open surgery as well as minimal invasive therapy, these two aspects are associated with the term "invasive neurotherapy".

However, in particular relating to different points in time, the terms "pre-operative" and "intra-operative" are used, relating to both aspects of the minimal invasive therapy and the open surgery. In other words, when using the term "operative" (or "pre-operative"), the present invention also relates to the other aspect of minimal invasive therapy, unless explicitly mentioned otherwise.

Thus, since the term "operation" includes any form of invasive therapy, the first 3D representation is acquired before the operation or intervention, and the second 3D representation is acquired during an intervention or an operation.

Figure 4:
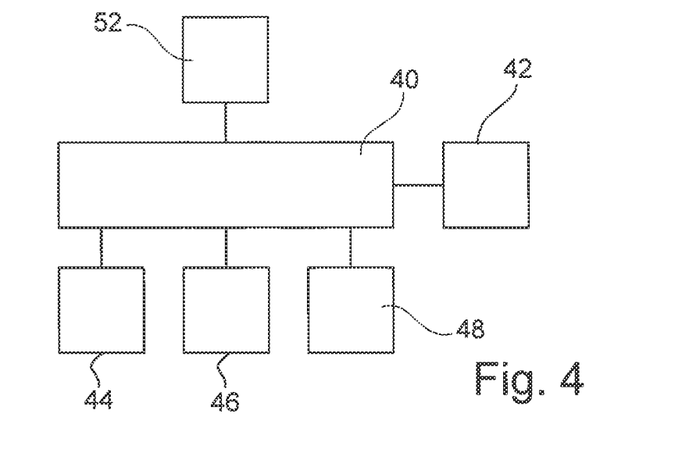

FIG. 4 shows a further example of the processing unit 40, which comprises an extrapolation unit adapted to extrapolate the determined vessel deformation to the brain structure representation. The brain structure representation comprises a vessel structure and a lobe structure comprising a number of convolutions in which the vessels are arranged. The application unit 48 is adapted to apply the deformation to the lobes only.

For the extrapolation, for example, mechanical parameters are considered, which can be based on pre- or intraoperative examination procedures.

The processing unit 40 can be adapted to translate or transform the deformation to the brain structure representation.

Figure 5:
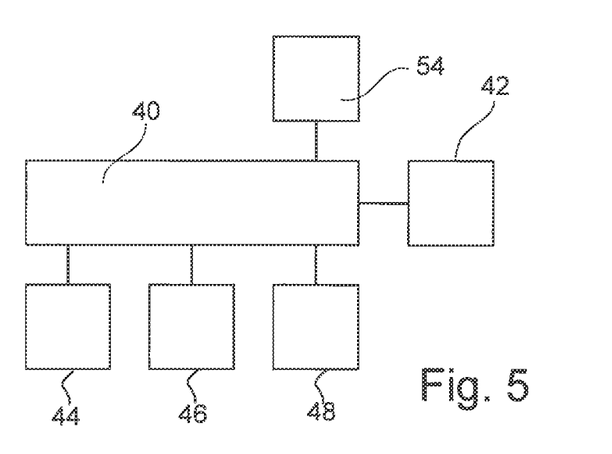

FIG. 5 shows a further exemplary embodiment, where the processing unit 40 comprises a generation unit 54 adapted to generate a deformation indicator from the deformation of the cerebral structure.

Figure 6:
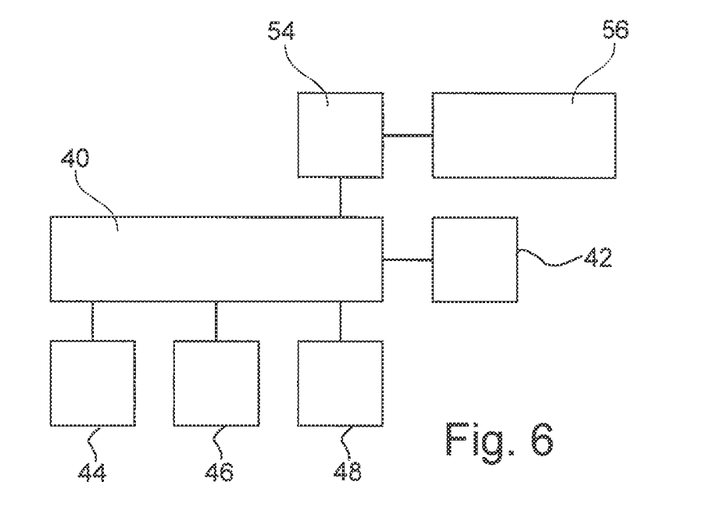

For example, a display unit 56 can be provided, as shown in FIG. 6, which is adapted to display the deformation indicator to a user.

For example, the display unit is adapted to show the representation of the brain with the actual or current deformation. The original planning can be then overlaid, for example.

According to a further aspect, not shown, the processing unit 40 is provided with a collision unit, which is adapted to provide collision indicators. These are indicating possible collisions of planned locations, for example a planned path, with predetermined brain structures, such as important lobe parts and/or important vessel parts or segments.

Figure 7:
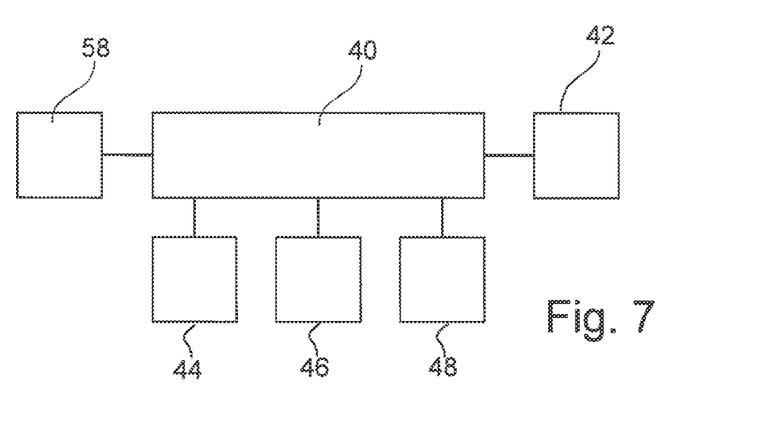

According to the example shown in FIG. 7, an interaction unit 58 is provided, which is adapted for a manual adjustment of the original planning by a user.

Figure 8:
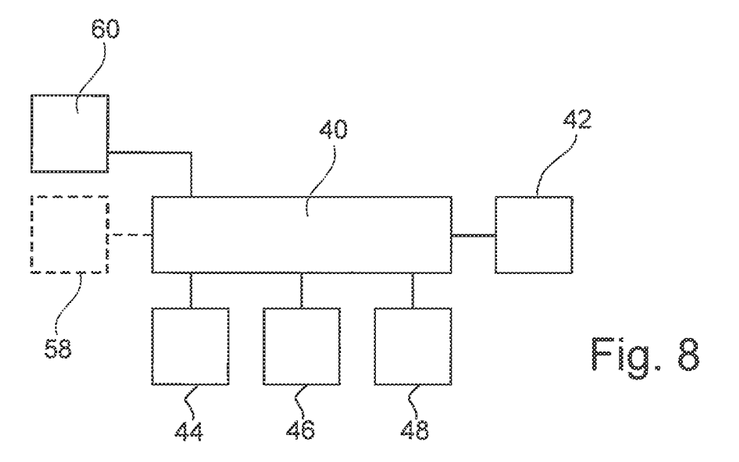

However, as shown in FIG. 8, the processing unit 40 can also be provided with an adjustment unit 60, which is adapted to automatically adjust the original planning, for example. The processing unit 40 is adapted to provide an adjustment indicator providing information of the grade of adjustment, for example on the display.

Indicators can be provided as a coloured coding. For example, grey-scale representation of the brain structure can be coloured at those regions where a deformation has been detected. Thus, a user can easily see where deformations have occurred. For example, in case of a rather strong deformation, wherein the term strong may relate to predetermined threshold values, is indicated with a red colour coding, whereas a light deformation is indicated with a yellow colour coding.

In case of planning data being adjusted to the current deformation, also such a coding can be applied, for example the planned path of an interventional device, such as a biopsy needle, is shown with a dark green line, and those parts of the path, which are adapted due to the determined deformation are shown with a bright green colour. Thus, a user can easily see where the planning data is amended, respectively adapted due to the deformation.

Figure 9:
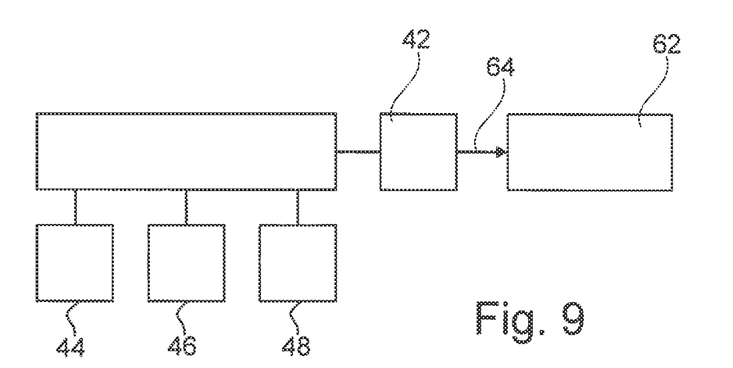

FIG. 9 shows an example of the device, wherein the interface unit 42 is adapted to provide the deformation adjusted planning data to an external navigation system 62. The data providing is indicated with an arrow 64 in the direction of the navigation system 62.

It must be noted that the above-mentioned examples of the FIGS. 2 to 9 can also be provided in combination with each other. In other words, one or more or even all of the examples can be combined in a device 12 for tracking brain deformation according to the present invention.

Before explaining the method examples according to the invention, some further aspects shall be discussed with reference to FIG. 1.

According to an exemplary embodiment, the X-ray image acquisition device is adapted to acquire the data for the first and the second 3D representations with the same imaging modality.

The device 12 for tracking brain deformation is shown in FIG. 1 together with a display arrangement 66, for example comprising one or more display units 56.

Further, interaction devices such as a keyboard 68, a mouse 70, a graphic tablet 72, as well as a further input device 74 are also shown, which are connected to the processing unit 40 of the device 12, wherein the processing unit 40 is not further shown in FIG. 1.

Figure 10:
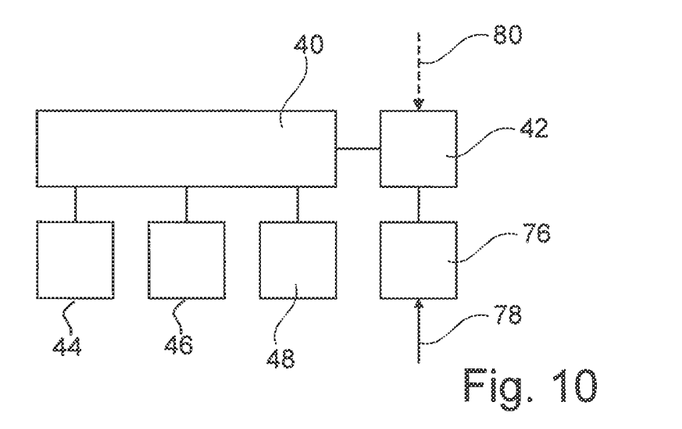

According to a further example, the processing unit 40 comprises a 3D image data generation unit 76, as indicated in FIG. 10. The 3D image data generation unit 76 is adapted to generate the first and second representation from the 3D X-ray image data. Thus, the 3D image data generation unit 76 is connected with the interface unit 42. In other words, with reference to FIG. 1, the image data provided by the X-ray image acquisition device 14 is provided to the 3D image data generation unit 76 where the generation of the representation takes place. The input of the image data provided by the X-ray image acquisition device is indicated in FIG. 10 with an arrow 78.

For example, the 3D image data generation unit 76 can be adapted to generate the data for the first 3D representation and the second 3D representation with the same processing steps.

Of course, in case of different 3D image data for the first and second representation, as provided by the X-ray image acquisition device 14, different processing steps can be provided.

According to a further example, not shown, the application unit 48 is adapted to apply the determined deformation of the cerebral structure to planning data for an intervention of the cerebral structure to generate deformation adjusted planning data. This is explained further below.

It must be noted further that the terms "register unit", "determination unit", "application unit", "mapping unit", "extrapolation unit", "generation unit", "3D image data generation unit", "adjusting unit", as well as the term "interface unit" can be provided as separate units in addition to the processing unit, but they might as well be provided as an integrated part of the processing unit itself, for example, one, a number, or even all of the above-mentioned units. This also applies for the above passages summarizing the invention.

According to a further exemplary embodiment, the interface unit 42 is adapted to provide at least one further 3D representation of a further cerebrovascular vessel structure. The further cerebrovascular vessel structure is based, for example, on a morphological brain scan and/or a functional brain scan. The application unit 48 can be adapted to apply the determined vessel deformation to the further cerebrovascular vessel structure, too. The input of a further cerebrovascular vessel structure to the interface unit 42 is indicated with a dotted arrow 80. It must be noted that this additional input is not an essential or necessary feature of the other aspects discussed in relation with FIG. 10. The input 80 is rather shown as an additional option that can also be applied to the other above described exemplary embodiments and aspects, for example those shown in FIGS. 2 to 9.

The further 3D representation that is deformed according the found deformation field, may come from an external source. For example, this may be the same type of dataset as the first 3D representation, but it does not need to be.

According to a further example, this dataset also does not need to contain the vessel structures. However, if this dataset is not identical to the first 3D representation, then the spatial mapping between those two is provided. This can be the case, because they are either acquired with the same machine, e.g., MRA and fMRI, or with a combined machine, e.g., PET-CT, or because a rigid or elastic registration has been performed between those two. It must be noted that this registration is an extra registration in addition to the one described above.

For example, the further 3D representation of the further cerebrovascular vessel structure is derived from an MRI imaging procedure or from a CT imaging procedure or a C-arm imaging procedure, using conebeam imaging.

For example, by applying the determined deformation also to the further cerebrovascular vessel structure, for example to the morphological brain scan or the functional brain scan, also these aspects or parameters can be provided to the user being adapted to the current deformation situation. In other words, according to the invention it is also possible to further improve and support the understanding of the current situation, on the side of a surgeon, for example. As mentioned above, the first 3D representation can be based on a pre-operative 3D X-ray scan and the second 3D representation can be based on an intra-operative 3D X-ray scan.

For example, the image data is acquired with a CT device or a C-arm device, for example as shown in FIG. 1.

The first representation can be generated from CTA (computed tomography angiography) 3D image data.

The first representation can also be generated from magnetic resonance angiography MRA 3D image data.

The first representation can also be generated from VasoCT 3D image data, wherein the VasoCT comprises 3D tomographic conebeam reconstruction with X-ray C-arm equipment, for example the equipment shown in FIG. 1.

Figure 11:
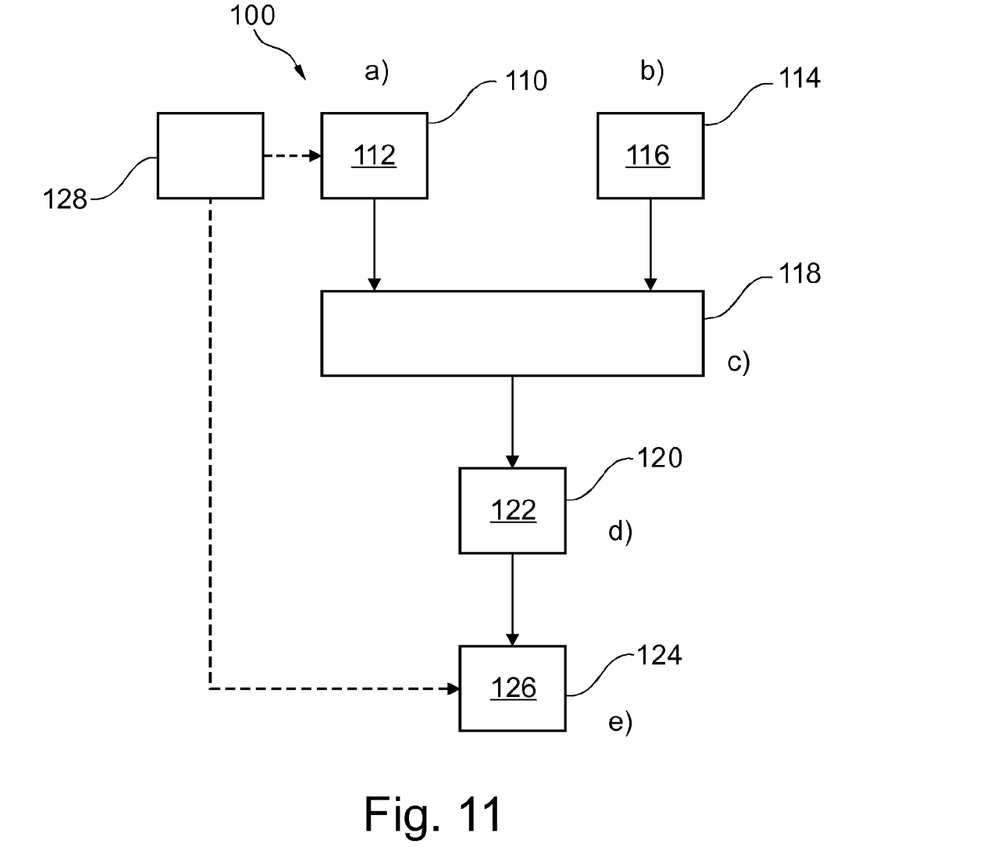
FIG. 11 illustrates basic steps of a method for tracking brain deformation according to an exemplary embodiment of the invention.

FIG. 11 shows a method 100 for tracking brain deformation, comprising the following steps: In a first provision step 110, a first 3D representation 112 of a cerebrovascular vessel structure of a region of interest of an object is provided. In a second provision step 114, a second 3D representation 116 of the cerebrovascular vessel structure is provided. Next, in a registration step 118, at least a part of the first 3D representation 112 is elastically three-dimensionally registered with at least a part of the second 3D representation 116.

Further, in a determination step 120, a deformation field 122 of the cerebrovascular vessel structure is determined, based on the elastic registration 118. Then, in an application step 124, the determined vessel deformation is applied to a brain structure representation to determine a deformation 126 of the cerebral structure.

The first provision step 110 is also referred to as step a), the second provision step 114 as step b), the elastic registration step 118 as step c), the determination step 120 as step d), and the application step 124 as step e).

In the elastic registration step, a predetermined part or region can be used for registration. For areas in between elastically registered parts, the deformation can be estimated based on the elastic registration results. The registration can be focussed on certain parts indicative of important deformation behaviour, for example as derived from previous examinations.

Of course, the elastic registration can also be performed for the complete 3D representation.

For example, the brain structure representation used in step e), can be provided from an initial image data acquisition step 128, from which, for example, the first 3D representation 112 is being generated or processed.

However, this initial step 128 is not a necessary part for the above-mentioned method, and thus, the connection of the initial step 128 to the first provision step 110, as well as the connection from the initial step 128 to the application step 124 is shown with dotted arrows only.

For example, the first 3D representation 112 is based on pre-operative image data and the second 3D representation 116 is based on intra-operative image data.

Figure 12:
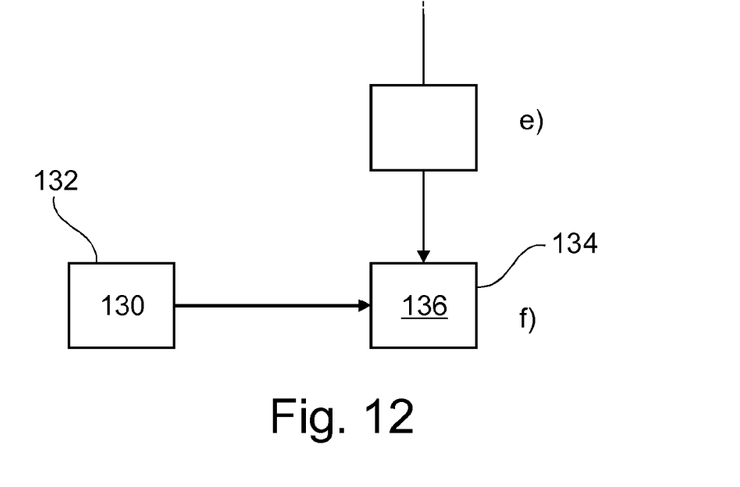

FIG. 12 shows a further exemplary embodiment of a method, in which planning data 130 for an intervention of the cerebral structure is provided in third provision step 132, and wherein, following step e), a step f) is provided in which the determined deformation of the cerebral structure is applied to the planning data in a second application step 134, to generate deformation adjusted planning data 136.

The planning data may be related to an intervention, such as a biopsy intervention, for example the planning data comprises intervention planning data.

The planning data can also be related to an operation, for example the planning data comprises operative planning data.

Step f) may comprise the generation of deformation compensated operative planning data.

Figure 13:
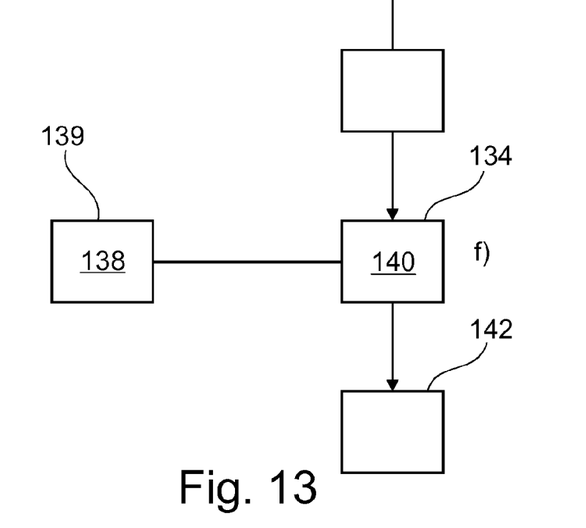

For example, the planning data may comprise course data 138, as shown in FIG. 13, which is provided 139 to the second application step 134 to generate deformation adjusted course data 140. The latter is provided in a further provision step 142 to a system for steering an interventional device, for example. The steering system may comprise automatically controlling a biopsy needle insertion or a brain punctuation device.

Figure 14:
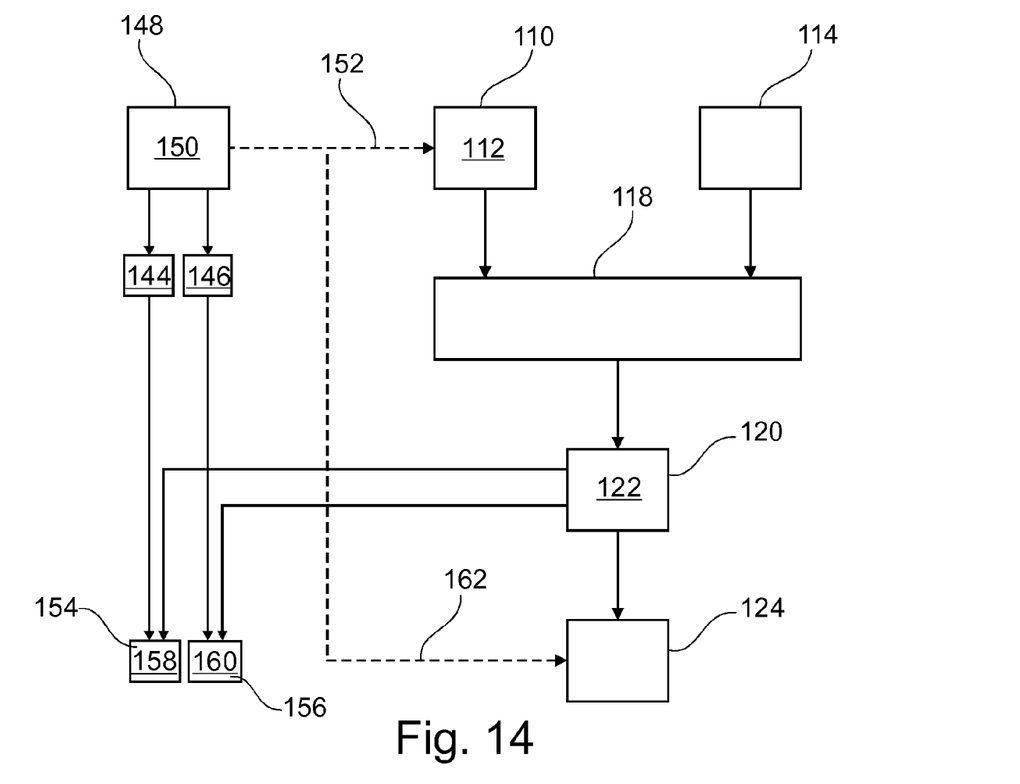

As already indicated above, pre-operative anatomical data 144 and/or functional data 146 can be provided for the region of interest, as shown in FIG. 14. The anatomical data 144 and/or the functional data 146 can be derived from an initial data acquisition step 148. For example, the first 3D representation 112 can also be derived from this initial acquisition step 148, where the respective image information 150 is acquired. Once again, the connection between such an initial acquisition step and the first provision step 110 is indicated with a dotted line 152, to indicate that this is a possible option, but not a necessity.

Further, the determined deformation field 122 from a determination step 120 can be applied to the anatomical data 144 and/or the functional data 146 in a further application step 154 and 156, respectively.

Thus, deformation adjusted anatomical data 158 and/or deformation adjusted functional data 160 can be generated.

As also indicated in FIG. 14, the image data acquired in the initial acquisition step 148 can also be used for providing the brain structure representation for the application step 124. This is indicated with a further dotted arrow 162.

With reference back to FIG. 11, the elastic registration step 118 may be image based or model based.

Step c) may comprise an elastic registration of other brain structures based on their voxel values. Step e) may comprise the determination of a deformation field of the other brain structures.

The elastic registration may comprise the determination of local displacements of corresponding vessel areas, vessel portions, or vessel parts.

According to an example, the registration is achieved by registering landmark points in the first representation 112 with corresponding landmark points in the second representation 116.

For example, the landmark points are bifurcations in the cerebrovascular vessel structure. According to a further example, the landmark points can be pronounced curves in the cerebrovascular vessel structure, wherein the pronounced curves are predetermined sections of the cerebrovascular vessel structure.

Figure 15:
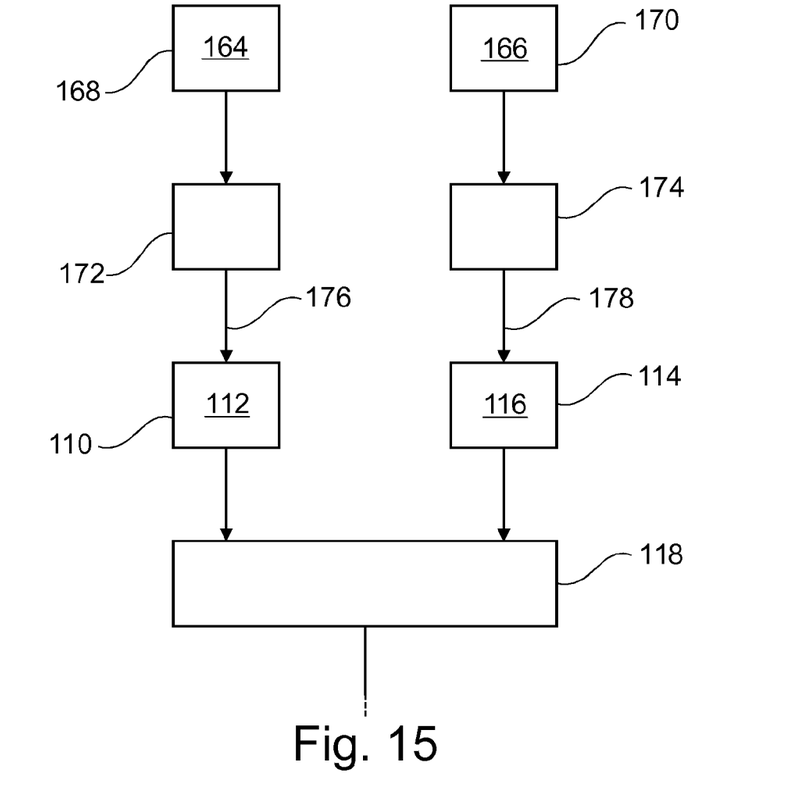

According to a further exemplary embodiment, shown in FIG. 15, the first 3D representation 112 and the second 3D representation 116 are provided by acquiring first and second 3D image data 164 and 166, respectively in a first and second image data acquisition step 168 and 170, respectively. The first and second 3D image data 164, 166 are each segmented in a segmentation step 172, 174, respectively, to the cerebrovascular vessel structures, indicated with an arrow 176 entering the first provision step 110 and a further arrow 178 entering the second provision step 114.

Thus, according to the example shown in FIG. 15, the vessel tree structure can be segmented.

Segmentation can also be achieved by segmenting the skull and performing a threshold procedure to the non-skull voxels.

Segmentation can also be achieved by segmenting the brain volume itself.

Further, segmentation can be achieved by applying a vessel filter to the dataset acquired and then applying a threshold procedure.

Segmentation can be achieved by applying a fast marching approach initiated by a user selected seed point.

The vessel structure may be used to generate the first and/or second representation of the cerebrovascular vessel structure.

According to a further example, not shown, in addition other structures can be segmented as well in the 3D dataset, for example the skull, and/or the cortex surface, and/or the ventricles, and/or the cerebellum, and/or the brain stem, and/or the cerebrospinal fluid, and/or the corpus callosum, and/or the left and right hemisphere.

Figure 16:
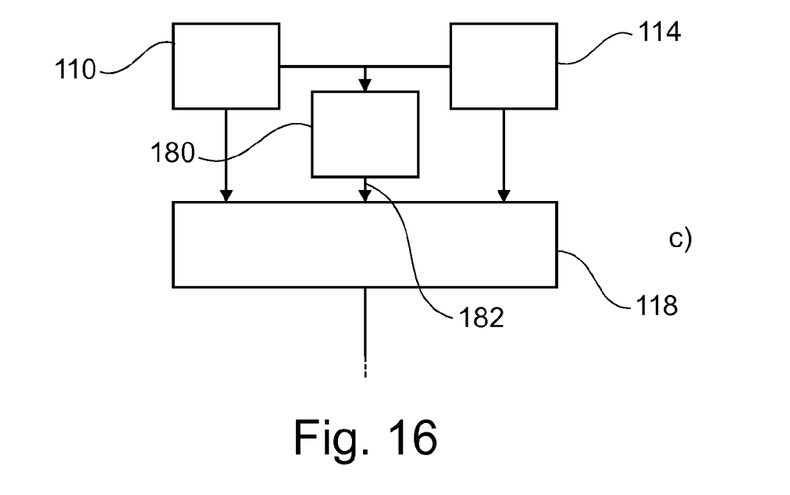

According to a further example, shown in FIG. 16, a rigid registration 180 is provided initialising the elastic registration step 118, i.e. initialising step c). The initialising is indicated with an arrow 182.

Figure 17:
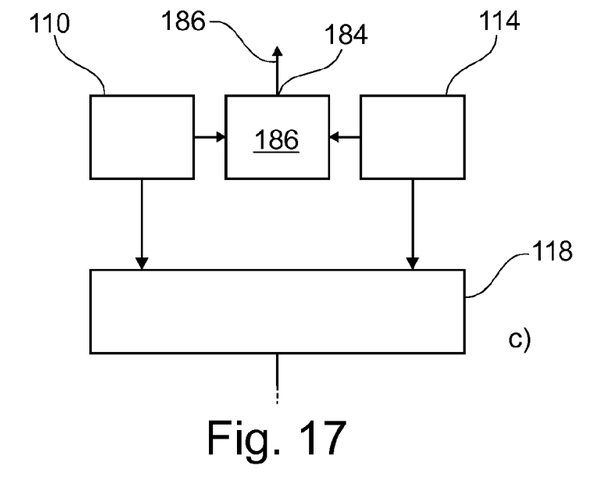

According to a further example, shown in FIG. 17, in addition to the elastic registration 118 in step c), a rigid registration step 184 is performed to determine global transformation data 186 of the cerebrovascular vessel structure. The global transformation data can be provided to a navigation system, for example for an automatic steering of a biopsy needle or brain punctuation device. The data supply is indicated with an arrow 186.

Figure 18:
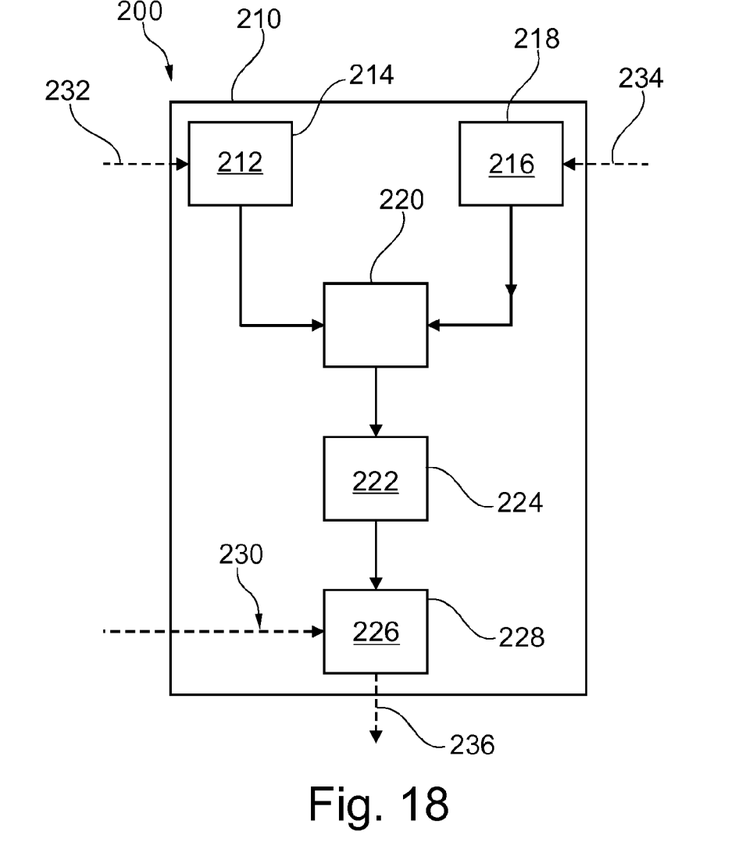

According to a further aspect of the invention, a method 200 of operating a device for tracking brain deformation is shown in FIG. 18. A processing unit 210 provides a first 3D representation 212 of a cerebrovascular vessel structure of a region of interest of an object in a first provision step 214. The processing unit further provides a second 3D representation 216 of the cerebrovascular vessel structure in a second provision step 218. Further, the processing unit 210 elastically three-dimensionally registers at least a part of the first 3D representation 212 with at least a part of the second 3D representation 216 in an elastic three-dimensional registration step 220. The processing unit 210 further determines a deformation field 222 of the cerebrovascular vessel structure based on the elastic registration in a determination step 224. Next, the processing unit 210 applies the determined vessel deformation 222 to a brain structure representation to determine a deformation 226 of the cerebral structure in an application step 228.

For example, the brain structure representation is provided to the processing unit 210, as indicated with dotted line arrow 230.

As further indicated in FIG. 18, the first and second 3D representations 212, 216 may also be provided to the processing unit as indicated with two respective dotted arrows 232 and 234.

According to a further example, the determined deformation 226 can then be provided to further purposes, as indicated with a dotted line arrow 236.

It must be noted that the first and second 3D representations of a cerebrovascular vessel structure can be based on image acquisition procedures using contrast agent. However, it is also provided to acquire the respective image information data without contrast agent.

According to a further aspect of the invention, the term "cerebrovascular vessel structure" relates to the vascular structure in the brain region.

According to a further aspect of the invention, a whole head scan containing the vessel structures is acquired at a pre-operative scan just before a clinical intervention starts, for example by MRA, CTA or VasoCT. One or more scans can then be performed during the course of the procedure. The vessel structures from those 3D image datasets are segmented and elastically co-registered onto each other. Since the vessels in the brain are contained within the convolutions, the local displacements of the vessel structures allow to accurately estimating the local brain deformation.

As mentioned above, the brain deformation may be used to adjust pre-procedural planning to the actual current situation. Furthermore, it may be fed into an external navigation system.

Figure 19A:
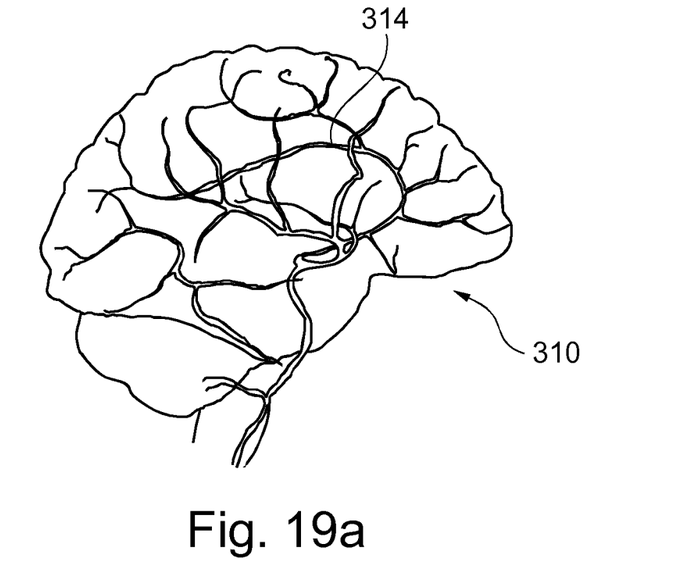
FIG. 19 illustrates a further aspect according to an exemplary embodiment of the invention.

For example, before a procedure, a pre-operative dataset is acquired with a large field of view, to contain the whole brain and the vasculature of the subject. From this data set, the vessel tree is segmented. An example for such a vessel tree 310 is shown in FIG. 19A. The vessel tree segmentation may be done in several ways, for example by segmenting the skull, for example using a model based approach, and perform a threshold to the non-skull voxels, and applying a connectivity criterion by only keeping the largest fully connected component. Or as another example, applying a vesselness-filter to the dataset and then applying a threshold. Or as a third example, applying a fast marching approach initiated by a user selected seed point.

Figure 19B:
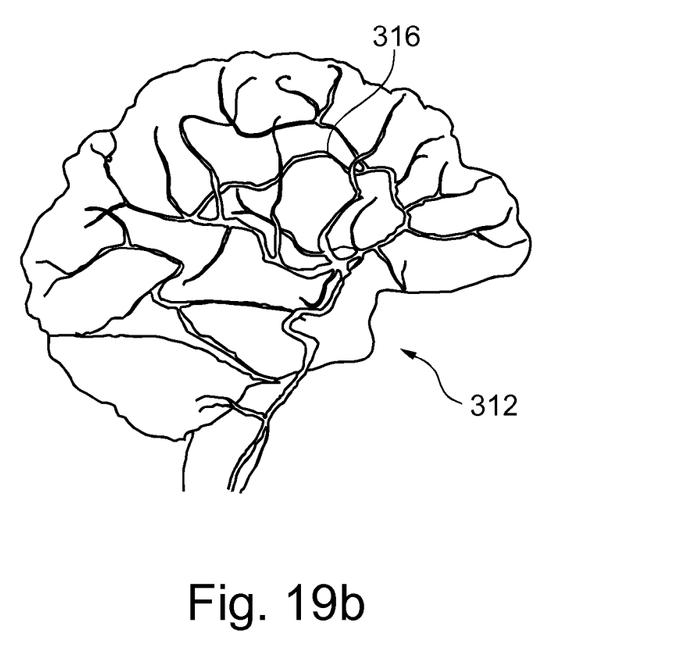

During the clinical procedure, a further dataset of the same subject is acquired and processed in the same manner, for example. Such a second vessel representation is shown in FIG. 19B. As can be seen, the second representation 312 shows a similar structure, however, certain regions show a deformation, for example the vessel part indicated with an arrow 314 in FIG. 19A has a different curvature in FIG. 19B, where the same vessel part is indicated with reference numeral 316.

It is noted that the drawings show fewer vessels than in a real scan would be visible, for simplicity reasons. Further, the representations in FIG. 19 have been exaggerated in relation to the deformation for clarity sake.

Then, as a so-to-speak third step, not shown, the deformation of the brain structure is determined based on the correspondences between the segmented vasculature in the pre-operative and intra-operative data set comprising 3D representations 310 and 312. This can be done in several ways, for example:

1. Per voxel, a number of vessel branches are selected, and the movement of a particular voxel is determined as a weighted average of the movements of the closest points in the selected vessel branches. The weighting may be the inverse of the distance to those points, but also another weighting function can be used. The selection of the vessel branches can be done based on their distance to the particular voxel, but also more sophisticated approaches are possible, for example determining in which brain lobe the voxel is situated, and including only the vessel branches that are adjacent to this lobe.

2. The deformation is determined by a mesh of tetrahedra. The tetrahedra are deformed by moving their nodes, and applying an interpolation scheme for the points inside the tetrahedra, yielding a weighted average of the displacement of the nodes, for example typically linear weighting. The tetrahedra nodes are placed on a regular grid, or on landmark points. The logical choice for the landmark points are points on the vessel centre lines, for example on a regular interval, or based on curvature, or on bifurcation points, or a combination of these.

3. A finite element driven approach, whereby the deformation is driven by the displacement of the vessel points and is modelled after the material properties of brain tissue are applied, for example globally, or based on a segmentation of a brain.

According to a further example, the segmentation and the above-mentioned elastic registration can be combined as single algorithm procedure.

Further, the acquisition of intra-operative image data, and thus the determination of a second 3D representation, as well as the elastic registration can be applied in a loop-like structure, i.e. repeated multiple times during a procedure.

As an option, the determined deformation of the brain can be applied to planning data.

Figure 20:
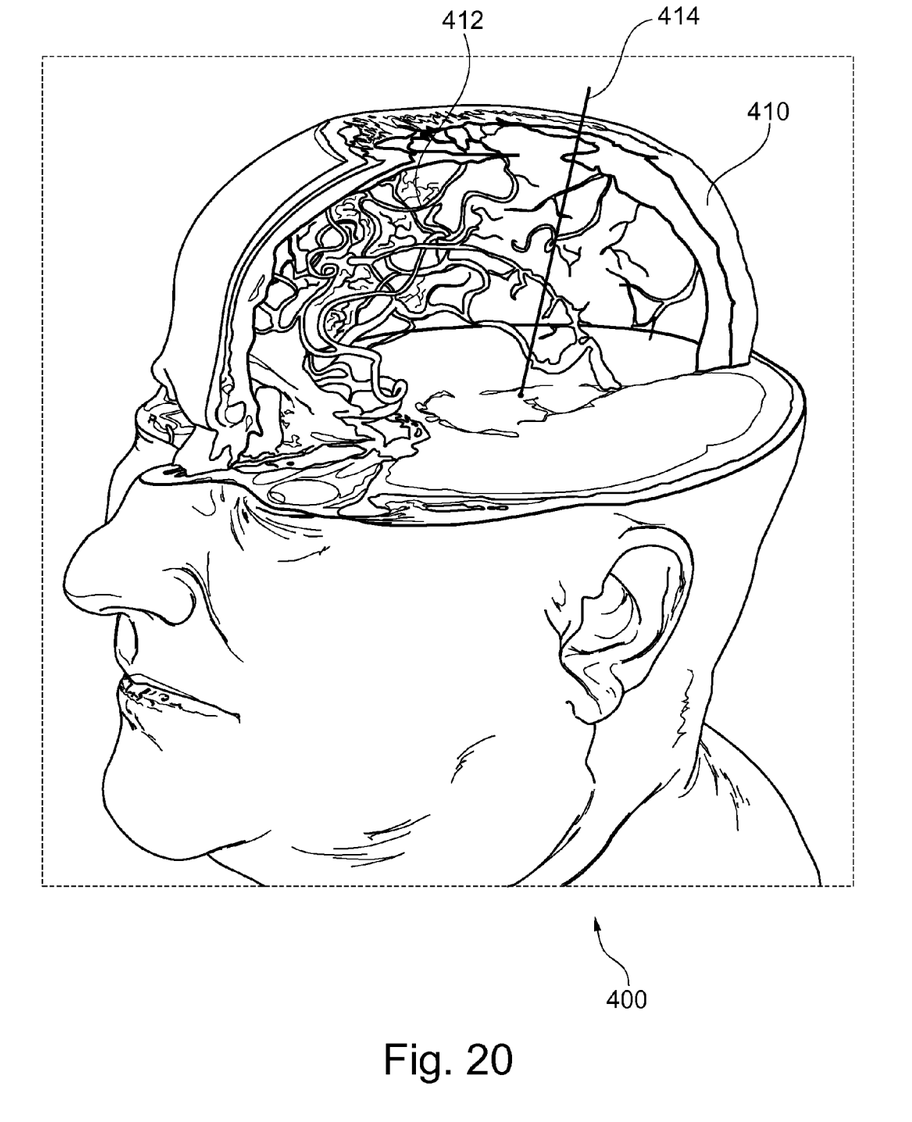
FIG. 20 shows a further aspect of a further exemplary embodiment according to the invention.

FIG. 20 shows a visualization of a patient's head 400. As can be seen, the brain is shown with a partly opened skull 410 and a vessel structure 412 inside the head, i.e. in the region where the brain is located. In this case, the brain structure itself is not further shown to visualize the respective vessel structure.

Further, an insertion path 414 is shown for an intervention with a biopsy needle, representing planning data. In case of a determined deformation of the brain, the respective representation, for example in form of the vessel representation 412, will be adapted or adjusted accordingly. The user could then see that his planned path 414 collides with one of the important structures, for example a vessel collision, with the puncture trajectory 414.

As a consequence, the user could then manually adjust the insertion path, i.e. the puncture trajectory, or perform an automatic adjustment of the planning data considering the found deformation. However, the deformation, and thus the adjustment of the vessel representation 412, is not further shown.

In another exemplary embodiment of the present invention (not shown), a computer program or a computer program element is provided i.e. characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention (not shown), a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

The invention claimed is:

1. A device for tracking brain deformation, the device comprising:
    a processor; and
    an image acquisition device that acquires and provides to the processor a first 3D representation of a cerebrovascular vessel structure of a region of interest of an object and a second 3D representation, which is based on X-ray image data, of the cerebrovascular vessel structure,
    wherein the processor:
        elastically three-dimensionally registers the first 3D representation with the second 3D representation,
        determines, after executing the elastic registration, a deformation field indicating vessel deformation of the cerebrovascular vessel structure based on the elastic registration of the first 3D representation with the second 3D representation, and
        applies the determined vessel deformation to a brain structure representation to determine a deformation of the brain structure.

2. The device according to claim 1, wherein the processor applies the determined deformation of the brain structure to planning data, for an intervention of the brain structure, to generate deformation adjusted planning data.

3. The device according to claim 1, wherein:
    the processor extrapolates the determined vessel deformation to the brain structure representation;
    the brain structure representation comprises a vessel structure and a lobe structure comprising a number of convolutions in which the vessels are arranged; and
    the processor applies the deformation to the lobes only.

4. The device according to claim 1, wherein:
    the image acquisition device acquires and provides to the processor a further 3D representation of a further cerebrovascular structure;
    the further cerebrovascular structure is based on a morphological brain scan or a functional brain scan; and
    the processor applies the determined vessel deformation to the further cerebrovascular structure.

5. The device according to claim 1, wherein:
    the processor generates a deformation indicator from the deformation of the brain structure; and the device further comprises:
    a display that displays the deformation indicator to a user.

6. The device according to claim 2, wherein the processor provides the deformation adjusted planning data to an external navigation system.

7. An imaging system for tracking brain deformation, the system comprising:
    the device according to claim 1, wherein
    the image acquisition device is an X-ray image acquisition device that acquires the second 3D representation as 3D X-ray image data in a contactless manner.

8. The imaging system according to claim 7, wherein:
    the X-ray image acquisition device is adapted to acquire the first and the second 3D representations with the same imaging modality; and
    the X-ray image acquisition device generates the first and the second 3D representations with the same processing steps.

9. A method for tracking brain deformation, the method comprising:
    a) acquiring, with an image acquisition device, a first 3D representation of a cerebrovascular vessel structure of a region of interest of an object;
    b) acquiring, with the image acquisition device, a second 3D representation of the cerebrovascular vessel structure that is based on X-ray image data;
    c) elastically three-dimensionally registering, with a processor, the first 3D representation with the second 3D representation;
    d) determining, with the processor after executing the elastic registration specified by operation (c), a deformation field indicating vessel deformation of the cerebrovascular vessel structure based on the elastic registration of the first 3D representation with the second 3D representation; and
    e) applying, with the processor, the determined vessel deformation to a brain structure representation to determine a deformation of the brain structure.

10. The method according to claim 9, further comprising:
    acquiring, with the processor, planning data for an intervention of the brain structure; and
    applying, with the processor and upon completing operation (e), the determined deformation of the brain structure to the planning data to generate deformation adjusted planning data.

11. A non-transitory computer readable medium comprising instructions executable by a processing device to cause an apparatus to perform the method of claim 9.

* * * * *